(12) United States Patent  
Samari

(10) Patent No.: US 7,833,482 B2  
(45) Date of Patent: Nov. 16, 2010

(54) LOW POWER COMBUSTIBLE GAS SENSOR

(75) Inventor: Ravosh Samari, Airdrie (CA)

(73) Assignee: Honeywell International Inc., Morristown, NJ (US)

( * ) Notice: Subject to any disclaimer, the term of this patent is extended or adjusted under 35 U.S.C. 154(b) by 813 days.

(21) Appl. No.: 11/617,947

(22) Filed: Dec. 29, 2006

(65) Prior Publication Data  
US 2008/0156076 A1 Jul. 3, 2008

(51) Int. Cl.  
G01N 31/12 (2006.01)  
G01N 27/16 (2006.01)  
G01N 7/00 (2006.01)  
G01N 9/00 (2006.01)

(52) U.S. Cl. ............................. 422/94; 422/95; 422/96; 422/97; 422/98; 73/23.31; 73/31.05

(58) Field of Classification Search .................... None  
See application file for complete search history.

(56) References Cited

U.S. PATENT DOCUMENTS

| | | | |
|---|---|---|---|
| 3,092,799 A | 6/1963 | Baker | |
| 3,200,011 A | 8/1965 | Baker | |
| 4,020,480 A | 4/1977 | Gofley | |
| 4,313,907 A | 2/1982 | McNally | |
| 4,416,911 A | 11/1983 | Wilkinson-Tough | |
| 5,599,584 A | 2/1997 | Champney | |
| 5,601,693 A | 2/1997 | Davies | |
| 5,813,764 A | 9/1998 | Visser | |
| 5,820,922 A | 10/1998 | Ricco | |
| 6,252,375 B1 | 6/2001 | Richter | |
| 6,348,872 B1 | 2/2002 | Otani | |
| 6,442,994 B1 | 9/2002 | Slater | |
| 6,742,382 B2 | 6/2004 | Warburton | |
| 2003/0159497 A1 | 8/2003 | Warburton et al. | |

FOREIGN PATENT DOCUMENTS

| | | |
|---|---|---|
| EP | 0 697 593 A1 | 2/1996 |
| WO | WO 00/14307 | 3/2000 |

OTHER PUBLICATIONS

Patent Cooperation Treaty International Search Report May 1, 2008.  
Patent Cooperation Treaty Written Opinion of the International Searching Authority May 1, 2008.  
P. Krebs and A. Grisel, A Low Power Integrated Catalytic Gas Sensor, Sensors and Actuators B, 13-14 (1993), 155-158.

Primary Examiner—In Suk Bullock  
Assistant Examiner—Neil Turk  
(74) Attorney, Agent, or Firm—Husch Blackwell LLP Welsh Katz

(57) ABSTRACT

A low power consumption catalytic gas sensor includes three beads. A trigger bead, which is smaller than either a sensing on a compensating bead can be monitored for the presence of a combustible gas. Where gas has been sensed, the sensing and compensating beads can be energized to establish a gas concentration.

6 Claims, 1 Drawing Sheet

LOW POWER COMBUSTIBLE GAS SENSOR

FIELD

The invention pertains to portable, battery powered detectors able to measure concentrations of combustible gases or vapors. More particularly, the invention pertains to such detectors which incorporate energy efficient catalytic sensors.

BACKGROUND

Combustible gas sensors employ catalytic combustion to measure combustible gases or vapors in air up to the Lower Explosive Limit (LEL) of the gas. Known sensors include a matched pair of elements, typically referred to as a detector and compensator (reference element). The detector comprises a platinum wire coil embedded within a bead of catalytic material. The compensator is similar except that the bead does not contain catalytic material and as a consequence is inert. Both elements are normally operated in a Wheatstone bridge circuit, which will produce an output only if the resistance of the detector differs from that of the compensator. The bridge is supplied with a constant dc voltage that heats the elements to 500-550° C.

Combustible gases are oxidized only on the detector element, where the heat generated increases its resistance, producing a signal proportional to the concentration of combustible gas. The compensator helps to compensate for changes in ambient temperature, pressure, and humidity, which affect both elements equally.

A catalytic bead sensor is typically operated at 500 degrees Celsius with a power consumption on the order of 200-350 mW. The temperature of 500 C is chosen in order to be able to detect all combustible gases such as methane and still have a reliable response across temperature, humidity, and maintain linearity across the full range of the sensor. Portable instruments that employ a catalytic sensor have restricted run-times and size due to the power requirements of the sensor.

It would be desirable to provide a miniature combustible gas detector that runs weeks at a time before charging the battery. Preferably the power requirements of such sensors could be reduced while maintaining the robustness, linearity and resistance to poisoning as is expected from current sensors.

DETAILED DESCRIPTION

Figure 1:
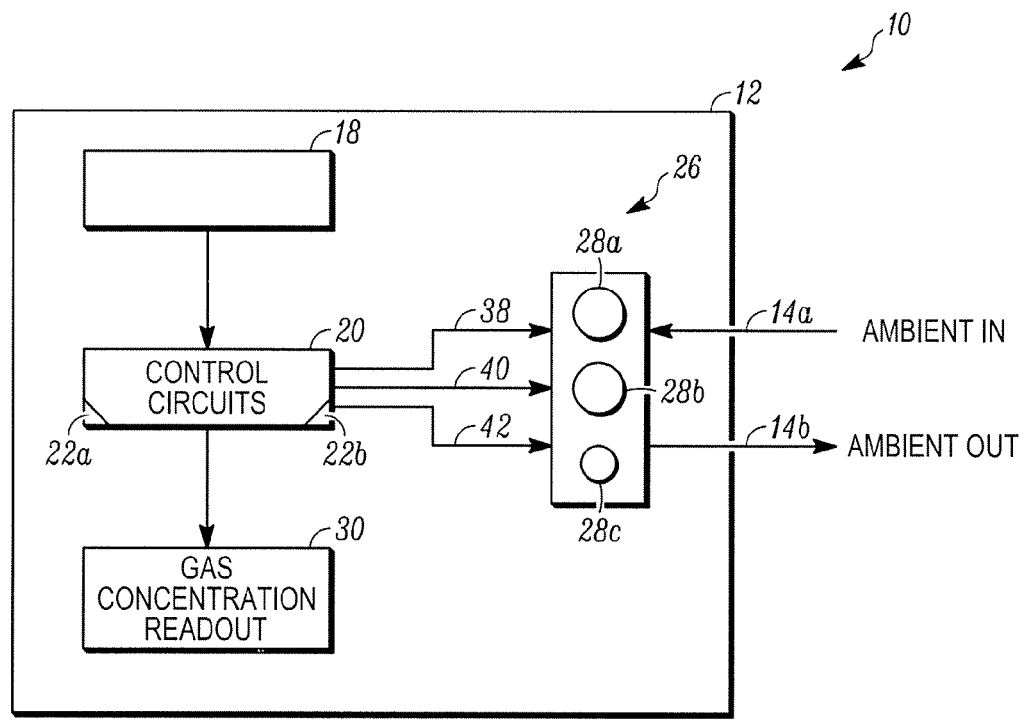
FIG. 1 is an overall block diagram of a detector which embodies the present invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

Embodiments of the invention include catalytic sensing and compensating beads. Additionally, a third bead called a trigger or a "sniff bead" which requires very little power has been added into the sensor. This bead is not required to be linear or immune to temperature/humidity fluctuations. With the restrictions of linearity and immunity to temperature and humidity fluctuations eliminated, the size and power restrictions of the "sniff" bead can dramatically be reduced in comparison to known detector beads which typically have a temperature 500 C.

The resistance of the trigger bead can be constantly or intermittently measured. If the resistance changes by a predetermined amount, the compensator/detector beads are turned on to provide an accurate and stable reading. The resistance change may arise from temperature humidity fluctuations or as a result of the trigger bead reacting to a combustible gas.

The last reading provided from the compensator/detector beads will be held until they are triggered to take a new reading. By adding the "sniff" bead, combustible sensors with power consumption on the order of 10 mW become feasible. This reduction in power enables users to run portable detectors for days without battery charging.

The addition of the third "sniff" bead which does not have the restraints of known detector beads has the advantage of reducing power consumption. The real-time measurement is not dependent on the third bead. The "sniff" bead just acts as a trigger to inform the sensor that something in the environment has changed, whether it is gas presence, humidity, or temperature changes.

FIG. 1 illustrates a portable, wearable if desired, form of a combustible gas detector 10. The detector 10 includes a housing 12 which has ports such as 14a, b which facilitate an inflow and an outflow of ambient atmosphere which may include one or more combustible gases whose concentration is to be determined.

Detector 10 includes an energy source 18, for example a replaceable or a rechargeable battery. Control circuits 20 are coupled to the power source 18. The control circuits 20 might be implemented at least in part with a programmable processor, such as 22a which executes software 22b which could be stored in a computer readable medium. Representative media include programmable read only memory, electrically erasable programmable read only memory as well as read write memory.

The control circuits 20 are in turn coupled to a multi-bead catalytic sensor indicated generally at 26. Sensor 26 incorporates a catalyzed sensing or detector bead of a type known to those of skill in the art 28a. Sensor 26 also includes a non-catalyzed compensating bead 28b. Finally, sensor 26 includes a trigger or "sniff" bead 28c.

Those of skill in the art will understand that the sensing and compensating beads, 28a, b are preferably linear in response and to the greatest extent possible immune to temperature and humidity fluctuations. The trigger or "sniff" bead 28c, in contradistinction, is not required to respond linearly or to be immune to temperature and humidity fluctuations.

In one embodiment of the invention, the control circuits 20 can couple predetermined amounts of electrical energy to the trigger or "sniff" bead 28c. Control circuits 20 can continually measure the resistance of the bead 28c. Where the resistance changes by a predetermined amount, for example due to the presence of a combustible gas whose concentration is to be measured, beads 28a, b can be energized and precise readings may be made as to the concentration of gas in the vicinity of the sensing bead 28a.

If desired, control circuits 20 can incorporate analog electrical bridges of the type known wherein sensing bead 28a is in one leg of the bridge and compensating bead 28 b is in a different leg of the bridge so as to provide a ratioing effect thereby eliminating temperature and humidity and similar environmental considerations which are common to both beads 28*a, b*. Alternately, where the control circuits include a processor, such as 22*a* and software 22*b* such processing can be carried out digitally based on sensing and compensating signals associated with the beads 28*a, b* which can be detected by the circuits 20.

Detector 10 can also include a visual readout 30 which can provide immediate visual feedback to the user or wearer of the detector 10 as to the concentration level of one or more predetermined combustible gases.

Figure 2:
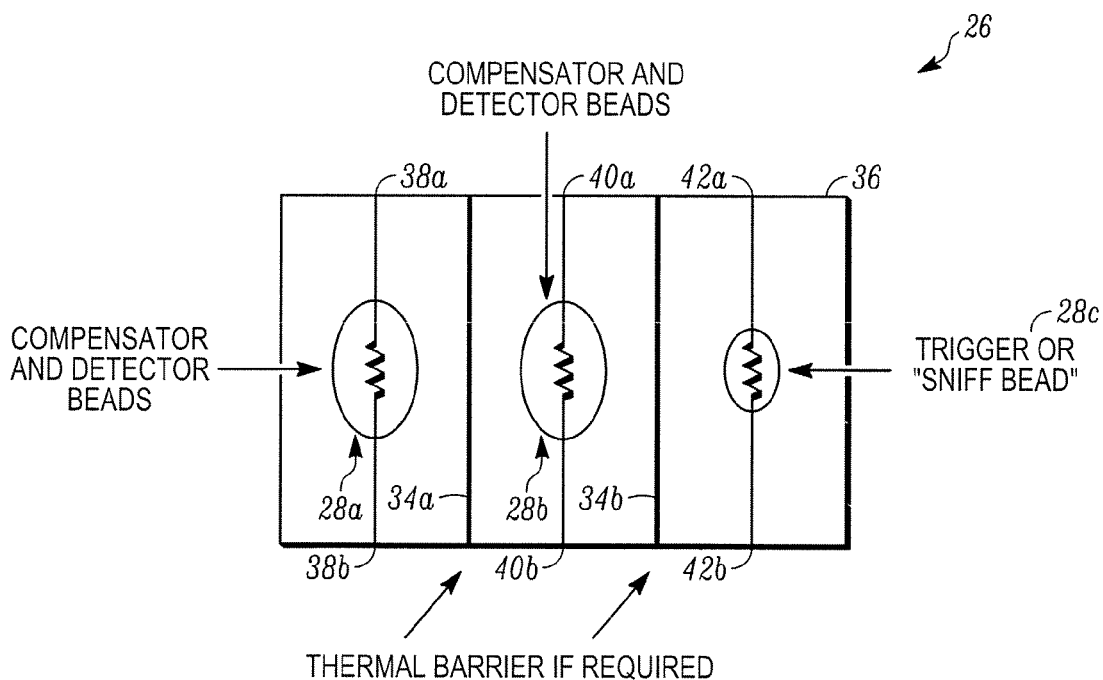
FIG. 2 is an enlarged view of a multi-bead sensor in accordance with the invention.

FIG. 2 illustrates additional details of the multi-bead sensor 26. The beads 28*a, b* and *c* can be spaced apart from one another by one or more thermal barriers 34*a, b* which are intended to minimize thermal cross talk effects from adjacent beads. The sensor 26 can include a base 36 which supports the beads as well as electrical terminations such as 38*a, b*, 40*a, b* and 42*a, b*. Conductors 38, 40 and 42, see FIG. 1, can be used to couple electrical energy from control circuits 20 to the respective contacts 38*a, b*, 40*a, b* and 42*a, b*. Additionally, signal lines 38, 40 and 42 can be monitored by circuits 20. Electrical parameters, such as resistance for example, of the respective beads 28*a, b* and *c* can be continuously or intermittently monitored for purposes of signal processing as described above.

Those of skill in the art will recognize that the "sniff" or trigger bead could be the same size, or even larger than the detector or compensator beads without departing from the spirit and scope of the invention. In that configuration, the trigger bead might operate at a higher power level than either of the other beads. Even in that instance, it is expected that there would still be a significant power savings over known two bead methods of operating such sensors.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A gas detector comprising:
  a combustible gas sensor having at least a catalyzed sensing bead, an uncatalyzed compensating bead, and a smaller catalyzed trigger bead; and
  control circuits coupled to the beads, which are configured to couple predetermined amounts of energy to the trigger bead, and which are configured to measure a resistance of the trigger bead, and which are configured to detect the measured resistance exceeding a predetermined value, so as to indicate a presence of a combustible gas, and which are configured to energize the sensing bead and compensating bead to measure a concentration of the combustible gas in response to the measured resistance exceeding the predetermined value.

2. A detector as in claim 1 where the trigger bead is energized at a level to produce a predetermined trigger signal in response to the presence of a predetermined concentration of a combustible gas.

3. A detector as in claim 2 where the control circuits are configured to energize the sensing bead and compensating bead at one level prior to receipt of the trigger signal and at a higher level, for at least a selected interval, subsequent to receipt of the trigger signal.

4. A detector as in claim 2 where the control circuits are configured to energize the sensing bead and compensating bead subsequent to receipt of the trigger signal.

5. A detector as in claim 4 where the control circuits are configured to energize the sensing bead and compensating bead intermittently.

6. A detector as in claim 5 where the sensing bead is coupled to an electrical bridge and intermittently energized so that the sensing bead operates in a diffusion limited state.

* * * * *